(12) United States Patent
Bhattacharya et al.

(10) Patent No.: US 8,852,128 B2
(45) Date of Patent: Oct. 7, 2014

(54) COMPUTER SYSTEM AND METHOD FOR ASSESSING DYNAMIC BONE QUALITY

(75) Inventors: Amit Bhattacharya, West Chester, OH (US); Nelson B. Watts, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 499 days.

(21) Appl. No.: 12/402,586

(22) Filed: Mar. 12, 2009

(65) Prior Publication Data

US 2009/0234251 A1 Sep. 17, 2009

Related U.S. Application Data

(60) Provisional application No. 61/035,884, filed on Mar. 12, 2008.

(51) Int. Cl.
*A61B 5/103* (2006.01)
*A61B 5/00* (2006.01)

(52) U.S. Cl.
CPC ............. *A61B 5/4509* (2013.01); *A61B 5/7257* (2013.01); *A61B 5/4504* (2013.01); *A61B 5/1038* (2013.01)
USPC ........... 600/587; 600/592; 600/594; 600/595; 482/8; 482/84; 482/86; 482/87; 482/88; 482/129; 482/133

(58) Field of Classification Search
USPC ................ 600/587, 592, 594, 595; 482/8, 84, 482/86–88, 90, 129, 133
See application file for complete search history.

(56) References Cited

U.S. PATENT DOCUMENTS

| | | | | |
|---|---|---|---|---|
| 3,169,022 A | * | 2/1965 | Kretsinger | 473/140 |
| 4,195,643 A | * | 4/1980 | Pratt, Jr. | 600/592 |
| 4,830,021 A | * | 5/1989 | Thornton | 600/520 |
| 4,928,959 A | * | 5/1990 | Bassett et al. | 482/79 |
| 5,081,991 A | * | 1/1992 | Chance | 600/411 |
| 5,273,028 A | * | 12/1993 | McLeod et al. | 601/35 |

(Continued)

FOREIGN PATENT DOCUMENTS

WO WO2008052367 5/2008

OTHER PUBLICATIONS

Huang et al, The effects of osteoarthritis on the biomechanical properties of the tibia, Chinese J. of Medical and Biological Engineering, 13(3):255-264 (1993) (English abstract only).

(Continued)

*Primary Examiner* — Sean Dougherty
(74) *Attorney, Agent, or Firm* — Jenei LLC

(57) ABSTRACT

A computer system for assessing dynamic bone quality is provided, including a memory that stores executable instructions, a central processing unit (CPU) capable of accessing the memory and executing the instructions to provide an output, and a receiver for receiving data input and transmitting it to the CPU, wherein the receiver is operably connected to: (1) a plurality of accelerometers, each accelerometer adapted to contact an exterior surface of a human subject at a load-bearing anatomical site and to receive input from each point of contact including acceleration response data; and (2) a force plate adapted to receive input including vertical ground reaction force data provided by a heel strike on the force plate, wherein the CPU executes the instructions to process the input data transmitted from the receiver to provide the output as a bone damping value. A method for assessing dynamic bone quality is also provided.

14 Claims, 7 Drawing Sheets

(56) References Cited

U.S. PATENT DOCUMENTS

| | | | |
|---|---|---|---|
| 5,376,065 A * | 12/1994 | McLeod et al. | 601/98 |
| 5,484,388 A * | 1/1996 | Bassett et al. | 601/27 |
| 5,524,637 A * | 6/1996 | Erickson | 600/592 |
| 5,603,325 A | 2/1997 | Mazess et al. | |
| 5,620,003 A * | 4/1997 | Sepponen | 600/527 |
| 5,623,944 A * | 4/1997 | Nashner | 600/592 |
| 5,782,763 A | 7/1998 | Bianco et al. | |
| 5,836,876 A | 11/1998 | Dimarogonas | |
| 5,897,510 A | 4/1999 | Keller et al. | |
| 5,915,036 A | 6/1999 | Grunkin et al. | |
| 6,063,046 A * | 5/2000 | Allum | 600/595 |
| 6,213,958 B1 | 4/2001 | Winder | |
| 6,234,975 B1 * | 5/2001 | McLeod et al. | 600/552 |
| 6,301,964 B1 * | 10/2001 | Fyfe et al. | 73/510 |
| 6,364,837 B1 | 4/2002 | Mazess et al. | |
| 6,411,729 B1 | 6/2002 | Grunkin | |
| 6,513,381 B2 * | 2/2003 | Fyfe et al. | 73/510 |
| 6,561,991 B2 * | 5/2003 | McLeod et al. | 600/587 |
| 6,607,497 B2 * | 8/2003 | McLeod et al. | 600/595 |
| 6,665,617 B2 * | 12/2003 | Shobayashi | 702/14 |
| 6,699,207 B2 * | 3/2004 | Tasch et al. | 600/587 |
| 6,936,016 B2 * | 8/2005 | Berme et al. | 600/595 |
| 6,971,267 B2 * | 12/2005 | Kawai et al. | 73/379.01 |
| 7,120,225 B2 | 10/2006 | Lang et al. | |
| 7,283,940 B2 | 10/2007 | Ascenzi et al. | |
| 7,402,142 B2 * | 7/2008 | Kawai et al. | 600/587 |
| 7,527,023 B2 * | 5/2009 | Davies | 119/712 |
| 7,673,587 B2 * | 3/2010 | Davies | 119/712 |
| 2002/0055691 A1 * | 5/2002 | Tasch et al. | 600/587 |
| 2002/0077567 A1 * | 6/2002 | McLeod et al. | 600/587 |
| 2004/0116836 A1 * | 6/2004 | Kawai et al. | 600/595 |
| 2004/0158174 A1 * | 8/2004 | Tasch et al. | 600/587 |
| 2005/0010106 A1 | 1/2005 | Lang et al. | |
| 2005/0010139 A1 * | 1/2005 | Aminian et al. | 600/595 |
| 2005/0197576 A1 | 9/2005 | Luo et al. | |
| 2005/0240086 A1 * | 10/2005 | Akay | 600/300 |
| 2006/0000420 A1 * | 1/2006 | Martin Davies | 119/174 |
| 2006/0155186 A1 | 7/2006 | James | |
| 2006/0251334 A1 * | 11/2006 | Oba et al. | 382/275 |
| 2007/0000216 A1 * | 1/2007 | Kater et al. | 54/1 |
| 2007/0130893 A1 * | 6/2007 | Davies | 54/1 |
| 2007/0133739 A1 | 6/2007 | Hangartner et al. | |
| 2007/0204802 A1 * | 9/2007 | Davies | 119/712 |
| 2007/0232963 A1 * | 10/2007 | Talish et al. | 601/2 |
| 2007/0250286 A1 * | 10/2007 | Duncan et al. | 702/139 |
| 2008/0021352 A1 * | 1/2008 | Keegan et al. | 600/595 |
| 2008/0031412 A1 | 2/2008 | Lang et al. | |
| 2008/0045804 A1 * | 2/2008 | Williams | 600/300 |
| 2008/0058613 A1 | 3/2008 | Lang et al. | |
| 2008/0058779 A1 | 3/2008 | Hipsley et al. | |
| 2008/0119719 A1 | 5/2008 | Ascenzi et al. | |
| 2008/0119763 A1 * | 5/2008 | Wiener | 600/587 |
| 2008/0125653 A1 | 5/2008 | Antich et al. | |
| 2008/0139977 A1 * | 6/2008 | Talish et al. | 601/46 |
| 2008/0194952 A1 | 8/2008 | Luo et al. | |
| 2008/0285805 A1 * | 11/2008 | Luinge et al. | 382/107 |
| 2009/0030344 A1 * | 1/2009 | Moser et al. | 600/587 |
| 2009/0062092 A1 * | 3/2009 | Mortimer et al. | 482/142 |

OTHER PUBLICATIONS

Bhattacharya, Dynamic bone quality—a non-invasive measure of bone's biomechanical property, Poster No. 107—Assessment of Bone Quality, Abstract in Journal of Clinical Densitometry: Assessment of Skeletal Health, 11:449-450 (2008).

Bhattacharya et al, Dynamic bone quality: a non-invasive measure of bone's biomechanical property in osteoporosis, Journal of Clinical Densitometry: Assessment of Skeletal Health, 13(2):228-236 (2010).

Alexander et al, Biomechanical aspects of preclinical descriptors of osetoarthritis, Abstract in J. of Biomechanics (1987), Presented at the combined 10th annual conference of American Society of Biomechanics, and the 4th biannual conference of the Canadian Society for Biomechanics, Montreal, CA, Aug. 25-27, 1986.

Bhattacharya et al, Bone quantity and quality of youths working on a farm—a pilot study, Journal of Agromedicine, 12(4)27-38 (2007).

* cited by examiner

COMPUTER SYSTEM AND METHOD FOR ASSESSING DYNAMIC BONE QUALITY

RELATED APPLICATION

This application claims priority to U.S. Provisional Patent Application No. 61/035,884, filed Mar. 12, 2008, which application is hereby incorporated by reference in its entirety.

FIELD OF THE INVENTION

The present invention relates to the field of bone screening and diagnosis. Specifically, the invention relates to a computer system and method for assessing dynamic bone quality in a human subject by measuring the bone shock absorption properties of the bone under realistic, in vivo loading conditions.

BACKGROUND OF THE INVENTION

Osteoporosis has a significant impact on the population of the United States, with more than 10 million people affected by the disease and 24 million at risk. Osteoporosis is associated with decreased bone mass and deterioration of the trabecular architecture of the bone, which collectively impact the bone's mechanical properties. Often, this degenerative disease leads to bone fracture (2 million per year), with associated costs exceeding $16 billion annually. Traditionally, measurement of bone mineral density (BMD) has been the predominant diagnostic and screening tool for osteoporosis and other degenerative bone diseases.

Dual energy x-ray absorptiometry, or DXA, is the most popular current method of assessing bone density. In this method, a subject is exposed to low-dose x-rays having two distinct energy peaks, with different characteristics in soft tissue and bone. Subtraction of the soft tissue absorption allows quantification of BMD. The procedure is carried out while the subject is at rest, thus providing BMD data for the bone under static conditions.

However, structural failure of the human bone rarely occurs under static conditions. A better understanding of bone fracture and prevention requires measurement of the biomechanical properties of the bone when exposed to realistic, in vivo loading—that is, an assessment of "dynamic" bone quality.

The transmission, absorption and attenuation of energy that intakes to the skeleton due to heel strike is an important component of bone physiology and pathology. The human locomotion system, which consists of natural shock absorbers (joints with viscoelastic components, articular cartilage, meniscus, intervertebral disks, trabecular bone, etc.), is subjected to constant loading and impact not only during weight lifting activities but also during normal daily activities such as walking, running, stair-climbing, etc. During heel strike, the vertical force component acting on the foot is on the order of 1.5 times the body weight depending upon walking velocity. These force waves are gradually attenuated by the body's natural shock absorbers on their way toward the head. The process of force wave attenuation is the body's natural way of protecting the most vital organ, the brain.

Among all natural shock absorbers in the human body, the trabecular bone has the highest capacity (170 times higher than that of cartilage) to attenuate incoming shock waves associated with heel-strike during walking and running. Since osteoporosis is associated with decreased bone mass and deterioration of trabecular architecture of the bone, the disease detrimentally changes the bone's natural shock absorbing capacity. The need exists to develop non-invasive, economical tools for assessing and monitoring dynamic bone quality.

The present invention is directed to a computer system and method for quantifying bone shock absorption (BSA) under dynamic conditions in order to assess the dynamic bone quality in a subject. The BSA variable, bone damping ($\zeta$), is a sensitive measure of the bone's structural integrity, a useful diagnostic of osteoporosis, and a valuable indicator of fracture risk.

SUMMARY OF THE INVENTION

Bone shock absorption (BSA), as expressed in the measurement of bone damping, is a useful tool in diagnosing osteoporosis and assessing dynamic bone quality.

Accordingly, it is an object of the present invention to provide a computer system for assessing dynamic bone quality, the system comprising:

a memory that stores executable instructions;

a central processing unit (CPU) capable of accessing the memory and executing the instructions to provide an output; and a receiver for receiving data input and transmitting it to the CPU;

wherein the receiver is operably connected to:

(1) a plurality of accelerometers, each accelerometer adapted to contact an exterior surface of a human subject at a load-bearing anatomical site of the subject and to receive input from each point of contact comprising acceleration response data; and (2) a force plate adapted to receive input comprising vertical ground reaction force data provided by a heel strike on the force plate;

wherein the CPU executes the instructions to process the input data transmitted from the receiver to provide the output as a bone damping value.

It is a further object of the present invention to provide a method for assessing dynamic bone quality in a human subject, the method comprising the steps of:

(a) contacting at least one accelerometer to an exterior surface of a human subject at a load-bearing anatomical site of the subject;

(b) directing the subject to strike a heel on a force plate;

(c) measuring vertical ground reaction force due to the heel strike;

(d) measuring an acceleration response at each of the accelerometers;

(e) processing the vertical ground reaction force and acceleration responses at a CPU to determine a bone damping value; and (f) comparing the bone damping value to a reference value to assess dynamic bone quality in the human subject.

These and other objects, features, and advantages will become apparent to those of ordinary skill in the art from a reading of the following detailed description and the appended claims.

DETAILED DESCRIPTION OF THE INVENTION

Figure 1:
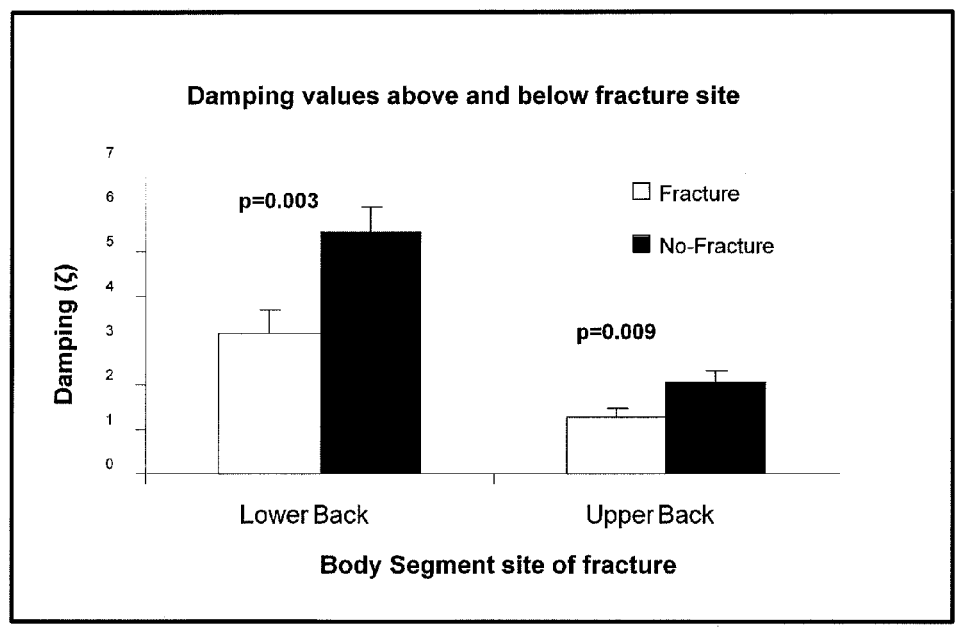
FIG. 1. Damping values above and below fracture site for fracture and non-fracture subjects with osteoporosis. Absolute damping value of the fracture group was significantly lower than that of the non-fracture group for the lower back ($p=0.003$) and upper back ($p=0.009$) regions.

The following is a list of definitions for terms used herein.

The term "dynamic bone quality," as used herein, refers to the bone shock absorption properties of the bone when exposed to in vivo loading. Dynamic bone quality can be assessed by measuring the damping properties of load-bearing bones and expressed as a bone damping value.

The term "damping," as used herein, refers to the ability of any structure to reduce the amplitude of oscillations in an oscillatory system, thus absorbing an applied shock wave. "Bone damping," as used herein, refers to the ability of a bone to absorb an applied shock wave. In the context of the human musculoskeletal structure, such a shock wave may be produced, for example, by a heel strike. However, one skilled in the art will appreciate that bone damping occurs and can be measured in response to any shock applied to the musculoskeletal structure of the body.

The term "memory," as used herein, refers to integrated circuits that store information in electronic devices and includes both volatile and non-volatile memory.

The term "executable instructions," as used herein, refers to machine-executable instructions that are carried out by a central processing unit, or CPU, which accesses the memory in a computer system.

The term "central processing unit," or "CPU," as used herein, refers to an electronic circuit capable of accessing memory and executing computer programs stored therein.

The term "output," as used herein, refers to the result of data processing by a CPU. In one embodiment of the invention, the output is a bone damping value. In another embodiment, output can include dB down in the Fast Fourier Transform (FFT) responses at each load-bearing anatomical site; numbers of peaks in the FFT responses at each load-bearing anatomical site; area under the FFT response graphs at each load-bearing anatomical site; and resonance frequency from FFT response graphs at each load-bearing anatomical site. See Ewing, D. J., *Modal Testing Theory and Practice*, Research Studies Press Ltd., John Wiley and Sons, Inc. (1984). Output can be provided in a variety of ways, including, but not limited to, display on a computer screen or in a printed report.

The term "receiver," as used herein, refers to any device suitable for receiving acceleration response data from the accelerometers and ground reaction force data from the force plate and transmitting the same to the CPU.

The term "accelerometer," as used herein, refers to a sensor capable of measuring the rate of change in velocity of the object being tested. In one embodiment of the invention, a plurality of accelerometers is employed, each of which is operably connected to the receiver. Suitable accelerometers include, but are not limited to, wired accelerometers, wireless MEMS based nano-accelerometers, and combinations thereof.

The term "load-bearing anatomical site," as used herein, refers to anatomical sites that support body segment weights situated immediately above the site of interest. For example, the feet support the weight of the entire body; the knees support the weight of the body above the knees, and so forth. Examples of load-bearing anatomical sites suitable for use in the present invention include, but are not limited to, the shin, tibia, femur, and vertebrae. In one embodiment of the invention, accelerometers are contacted to exterior surfaces of the subject at the lower shin above the ankle, tibia, femur, third lumbar vertebra and seventh thoracic vertebra.

The term "non-load-bearing anatomical site," as used herein, refers to an anatomical site that does not ordinarily support body weight. For example, the arms are generally non-load-bearing anatomical sites, unless a subject uses his arms to support body weight, such as in the event of a fall where the subject uses his arms to brace the impact. Another example of a non-load-bearing anatomical site is the head, and more particularly the forehead.

The term "acceleration response data," as used herein, refers to the measurement of raw acceleration versus time. Acceleration response data is produced by each accelerometer in response to an applied shock wave to the body, for example, after the subject completes a heel strike.

The term "force plate," as used herein, refers to an apparatus comprising sensors capable of measuring an applied force. Suitable force plates are commercially available, for example, from Advanced Mechanical Technology, Inc. (Watertown, Mass.). In a specific embodiment of the invention, the force plate is capable of measuring vertical ground reaction force generated by a heel strike.

The term "vertical ground reaction force data," as used herein, refers to a reaction force generated in response to an applied force. Consistent with Newton's Third Law, for every action there is an equal and opposite reaction. Thus, for example, when a subject strikes a force plate with his or her heel, a ground reaction force is generated. The force plate can capture this ground reaction force in vertical, horizontal, and lateral directions. In one embodiment of the invention, the vertical ground reaction force is measured and the vertical ground reaction force data is used to determine a bone damping value.

The term "heel strike," as used herein, refers to the act of striking a surface, such as a force plate, with the heel of the foot. For example, a subject can produce a heel strike by stepping or stomping on a force plate.

The term "reference value," as used herein, refers to an average bone damping value obtained from normal, healthy subjects. In one embodiment, the reference value for bone damping is a range of from about 18 to about 30. In another embodiment, the reference value is a range of from about 20 to about 27. In yet another embodiment, the reference value is a range of from about 22 to about 26. In yet another embodiment, the reference value for bone damping is about 24.

Computer System for Assessing Dynamic Bone Quality

Figure 3:
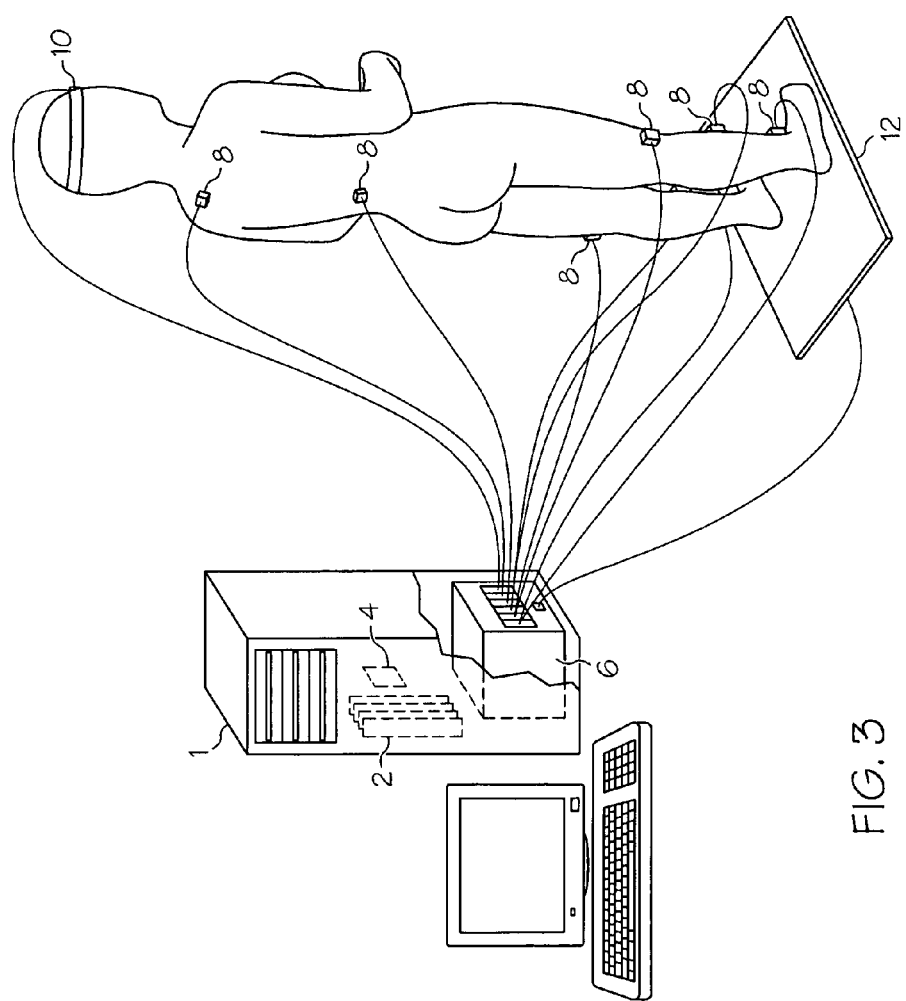
FIG. 3. An embodiment of a computer system of the present invention.

In one embodiment of the invention, a computer system 1 for assessing dynamic bone quality is provided, the system comprising: a memory 2 that stores executable instructions; a central processing unit (CPU) 4 capable of accessing the memory and executing the instructions to provide an output; and a receiver 6 for receiving data input and transmitting it to the CPU 4; wherein the receiver 6 is operably connected to: (1) a plurality of accelerometers 8, each accelerometer adapted to contact an exterior surface of a human subject at a load-bearing anatomical site of the subject and to receive input from each point of contact comprising acceleration response data; and (2) a force plate 12 adapted to receive input comprising vertical ground reaction force data provided by a heel strike on the force plate; wherein the CPU 4 executes the instructions to process the input data transmitted from the receiver 6 to provide the output as a bone damping value (see, for example, FIG. 3). Suitable load-bearing anatomical sites include, but are not limited to, the tibias, the femurs, and the vertebrae.

In another embodiment of the invention, the receiver 6 is operably connected to at least one accelerometer 10 adapted to contact an exterior surface of the subject at a non-load-bearing anatomical site of the subject. Suitable non-load-bearing anatomical sites include, but are not limited to, the head and forehead.

In one embodiment of the invention, the executable instructions comprise performing algorithms on the acceleration response data and the vertical ground reaction force data in order to determine a bone damping value, the algorithms selected from the group consisting Fast Fourier Transform (FFT), transfer function, and Frequency Response Function (FRF).

Figure 4:
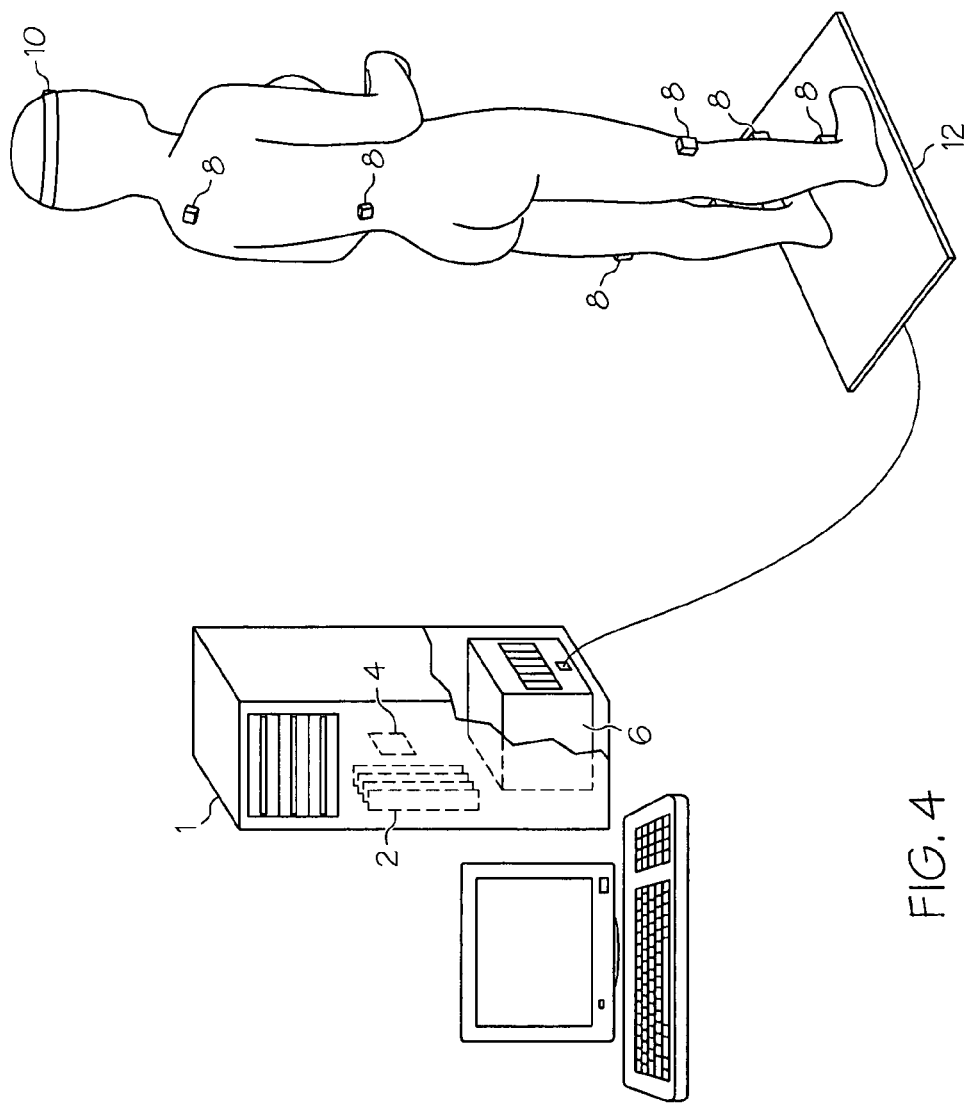
FIG. 4. An embodiment of a computer system of the present invention.

Many varieties of accelerometers are known in the art and suitable for use in the present invention. Indeed, any accelerometer capable of measuring acceleration response and transmitting acceleration response data from load-bearing and non-load-bearing anatomical sites may be used. In a specific embodiment, the accelerometers (located at either load-bearing or non-load-bearing anatomical sites) are selected from the group consisting of wired accelerometers, wireless accelerometers, MEMS based nano-accelerometers, and combinations thereof. In a more specific embodiment, the accelerometers are wireless MEMS based nano-accelerometers (see, for example, FIG. 4, illustrating a wireless embodiment of the computer system).

Method for Assessing Dynamic Bone Quality

In another embodiment of the invention, a method for assessing dynamic bone quality in a human subject is provided, the method comprising the steps of:

(a) contacting at least one accelerometer to an exterior surface of a human subject at a load-bearing anatomical site of the subject;

(b) directing the subject to strike a heel on a force plate;

(c) measuring vertical ground reaction force due to the heel strike;

(d) measuring an acceleration response at each of the accelerometers;

(e) processing the vertical ground reaction force and acceleration responses at a CPU to determine a bone damping value; and (f) comparing the bone damping value to a reference value to assess dynamic bone quality in the human subject.

In another embodiment, step (a) further comprises contacting at least one accelerometer to an exterior surface of a human subject at a non-load-bearing anatomical site of the subject, such as the forehead.

The bone damping value can be compared to a reference value, representing normal, healthy individuals, in order to assess dynamic bone quality. In one embodiment of the invention, a bone damping value lower than the reference value indicates a presence or risk of bone disease. In a specific embodiment, the bone disease is selected from the group consisting of osteoporosis, osteoarthritis, and bone fracture.

In another embodiment of the invention, the method further comprises determining a bone mineral density, or BMD, of the human subject. Suitable methods for determining BMD are well-known in the art. See, for example, "NIH Consensus Development Panel on Osteoporosis Prevention, Diagnosis, and Therapy," *Journal of the American Medical Association* 285: 785-95 (2001). In one embodiment, the BMD is determined by dual energy x-ray absorptiometry (DXA).

Many types of accelerometers are known in the art and suitable for use in the present invention. Indeed, any accelerometer capable of measuring acceleration response and transmitting acceleration response data from load-bearing and non-load-bearing anatomical sites may be used in the method. In a specific embodiment, the accelerometers are selected from the group consisting of wired accelerometers, wireless accelerometers, MEMS based nano-accelerometers, and combinations thereof. In a more specific embodiment, the accelerometers are wireless MEMS based nano-accelerometers.

In another embodiment of the invention, the processing step (e) comprises performing algorithms selected from the group consisting Fast Fourier Transform (FFT), transfer function, and Frequency Response Function (FRF).

Calculation of Bone Damping Value

Figure 6:
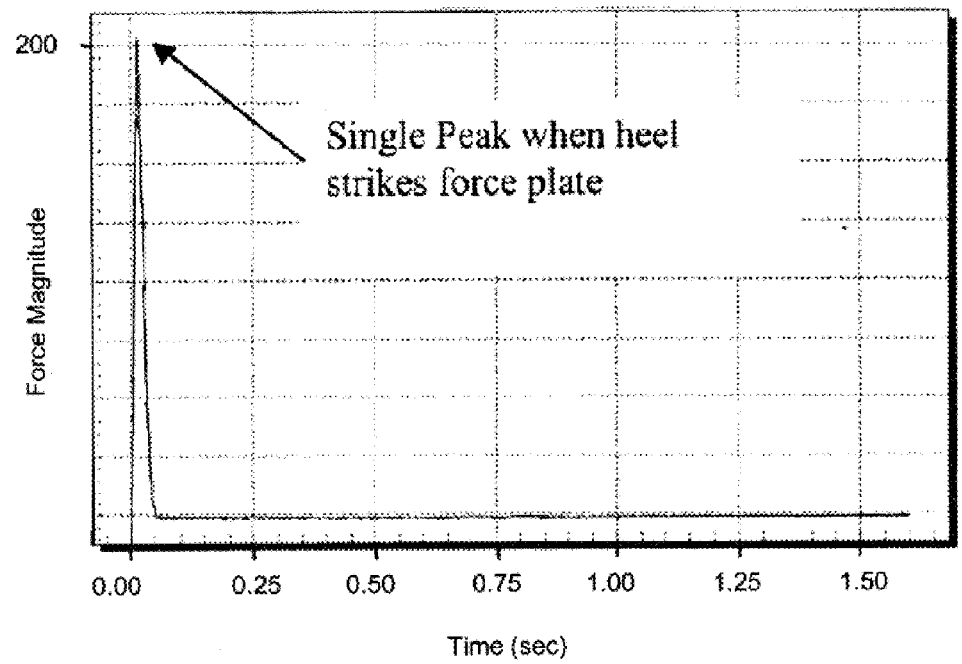
FIG. 6. Example of vertical ground reaction force data generated by a heel strike on a force plate.
Figure 7:
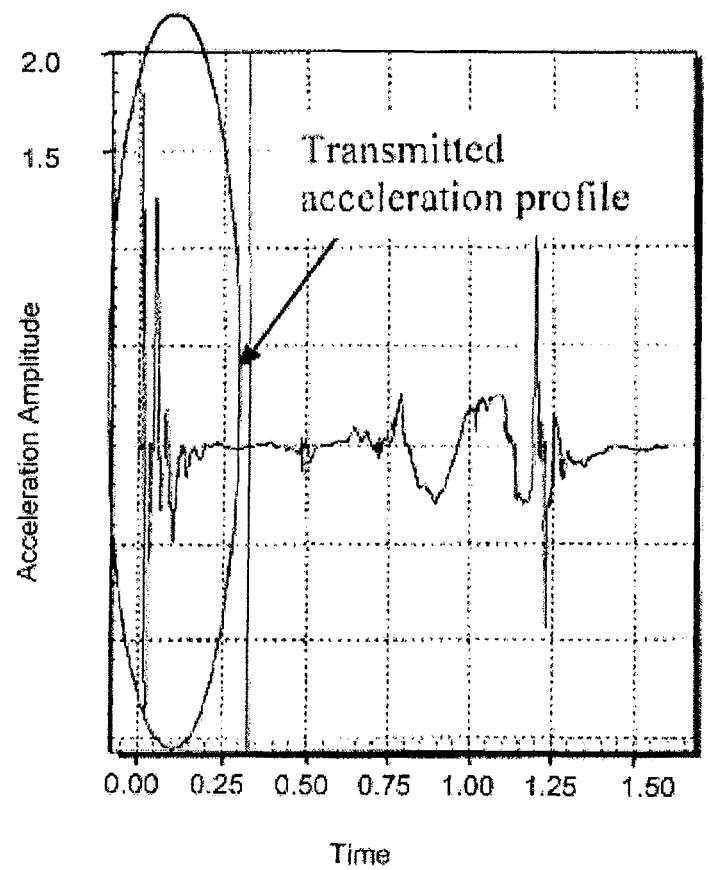
FIG. 7. Example of acceleration response data generated at a load-bearing anatomical site, in response to a heel strike.

Data collected from the force plate and accelerometers after heel strike are used to calculate the bone damping value for each anatomical site of interest. The force plate measures the time domain force profile created by the heel strike (the vertical ground reaction force data). See, for example, FIG. 6. Each accelerometer measures the time domain acceleration profiles caused by the heel strike (acceleration response data) at each anatomical site of interest. See, for example, FIG. 7. The data is transmitted to the computer system, programmed to determine the bone damping value at each anatomical site.

In order to determine bone damping, the musculoskeletal system is treated as a single degree of freedom system responding to the transient force due to heel strike. A Fast Fourier Transform (FFT) of the vertical ground reaction force data and the acceleration response data at all anatomical test sites is performed. The number of peaks in the frequency domain up to 100 Hz are considered for the analysis. The first dominant frequency and next four peaks in the increasing frequency direction are computed for acceleration waveforms at all anatomical sites. The frequency response function (FRF) of vertical ground reaction force and acceleration response are obtained using the following equation:

$$\text{FRF} = \text{FFT of acceleration response at an anatomical site/FFT of vertical ground reaction force.}$$

Damping value is obtained directly from the measured FRF using the structural bandwidth and resonance frequency method. See Ewing, D. J., *Modal Testing: Theory and Practice*, Research Studies Press Ltd., John Wiley and Sons, Inc. (1984) and Coleman, R E., *Experimental structural dynamics: An introduction to experimental methods of characterizing vibrating structures*, Author House (2004). By this method, the structural bandwidth is manifest in the FRF real part as the frequency separation between two extrema, symmetric about the resonance frequency, whereas the resonance frequency coincides with a single peak in the FRF imaginary part. The damping value is determined according to the following equation:

$$\text{Bone damping value } \zeta = (1/2)^*(\text{structural bandwidth/resonance frequency})$$

Using this equation, a bone damping value is determined for each anatomical site of interest.

Additional Outputs

Figure 5:
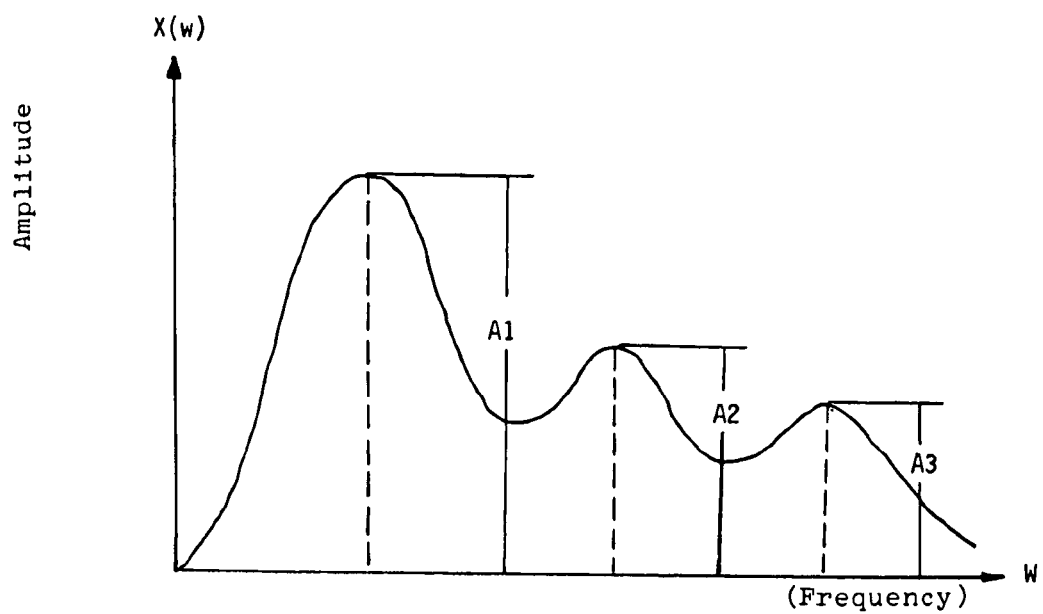
FIG. 5. Representation of acceleration response data in the frequency domain from an accelerometer.

Other outputs are also optionally provided by the system, including dB down in the Fast Fourier Transform (FFT)

curves corresponding to each load-bearing anatomical site; numbers of peaks in the FFT responses at each load-bearing anatomical site; area under the FFT response graphs at each load-bearing anatomical site; and resonance frequency from FFT response graphs at each load-bearing anatomical site.

dB down of an acceleration FFT curve is calculated according to the following method:

$$dB1 = 20 \log_{10}(A2/A1)$$

$$dB2 = 20 \log_{10}(A3/A1)$$

wherein A1, A2, and A3 are obtained from the FFT curve, as represented, for example, in FIG. 5.

EXAMPLES

The following examples are given by way of illustration, and are in no way intended to limit the scope of the present invention.

Example 1

A Caucasian, post-menopausal female subject has accelerometers placed in contact with load-bearing anatomical sites on the exterior surface of her body, the sites comprising the shin bones immediately above the ankles, the tibias, the lateral femoral condyles, the third lumbar vertebra, and the seventh thoracic vertebra. An additional accelerometer is contacted to her forehead, a non-load-bearing anatomical site. The subject is then instructed to strike her heel on the force plate. The force plate measures the time domain force profile created by the heel strike (the vertical ground reaction force data). Each accelerometer measures the time domain acceleration profiles caused by the heel strike (acceleration response data) at each anatomical site of interest. The data is transmitted to the computer system, which is programmed to determine the bone damping value at each anatomical site.

In order to determine bone damping, the musculoskeletal system is treated as a single degree of freedom system responding to the transient force due to heel strike. A Fast Fourier Transform (FFT) of the vertical ground reaction force data and the acceleration response data at all anatomical test sites is performed. The number of peaks in the frequency domain up to 100 Hz are considered for the analysis. The first dominant frequency and next four peaks in the increasing frequency direction are computed for acceleration waveforms at all anatomical sites. The frequency response function (FRF) of vertical ground reaction force and acceleration response are obtained using the following equation:

FRF=FFT of acceleration response at an anatomical site/FFT of vertical ground reaction force.

Damping value is obtained directly from the measured FRF using the structural bandwidth and resonance frequency method. By this method, the structural bandwidth is manifest in the FRF real part as the frequency separation between two extrema, symmetric about the resonance frequency, whereas the resonance frequency coincides with a single peak in the FRF imaginary part. The damping value is determined according to the following equation:

Bone damping value=(½*structural bandwidth)/resonance frequency

Using this equation, a bone damping value is determined for each anatomical site of interest. The bone damping value of the female subject at the right femoral condyle is 5.0, significantly lower than the bone damping value of a normal healthy adult. The bone damping data indicate the subject is suffering from osteoporosis and is at risk for developing bone fracture.

Example 2

Decreased Bone Shock Absorbing Capacity in Individuals with Bone Disease

Five groups of subjects undergo dynamic bone quality analysis, the groups including healthy adults (N=10), healthy youth (N=18), individuals with osteoporosis and without fracture (N=39), individuals with osteoarthritis (N=8), and individuals with osteoporosis and with fracture (N=28). Each individual has accelerometers placed in contact with load-bearing anatomical sites on the exterior surface of the body, the sites comprising the shin bones immediately above the ankles, the tibias, the lateral femoral condyles, the third lumbar vertebra, and the seventh thoracic vertebra. An additional accelerometer is contacted to the forehead of the test subjects, a non-load-bearing anatomical site.

Figure 2:
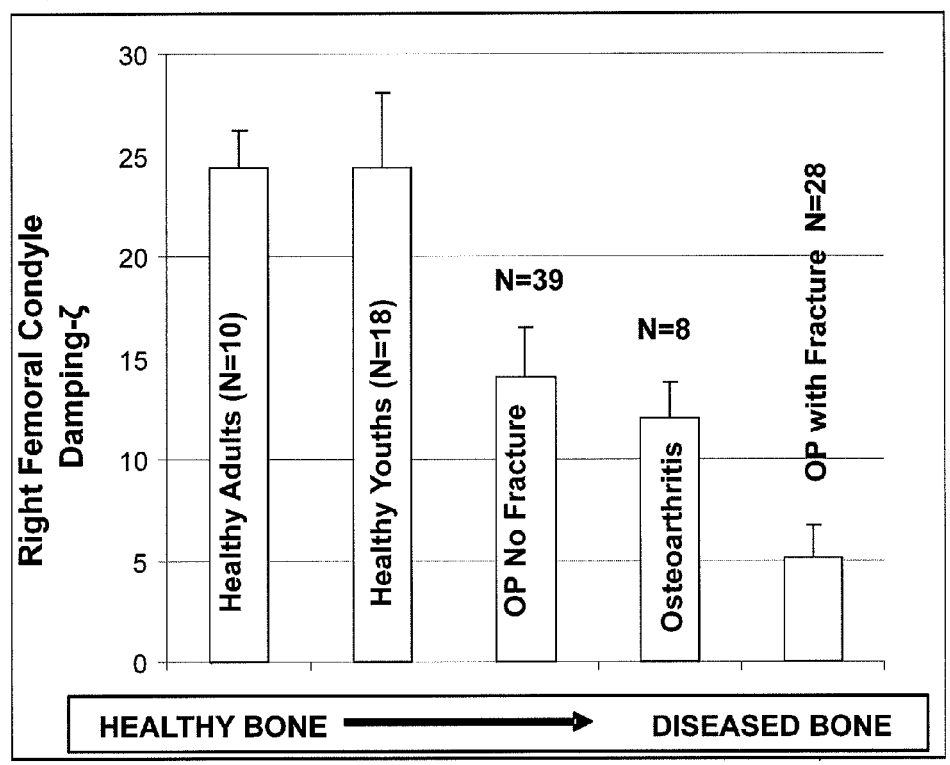
FIG. 2. Damping value data of right femoral condyle for five test groups: healthy adults, healthy youth, individuals with osteoporosis and without fracture, individuals with osteoarthritis, and individuals with osteoporosis and with fracture. Damping values are significantly different for all comparisons (p values ranging between 0.04 and 0.0001), except between healthy adults and healthy youth and individuals with osteoporosis without fracture and individuals with osteoarthritis.

Each individual is instructed to strike his or her heel on the force plate. Bone damping values are determined for each subject, corresponding to each anatomical site of interest. The data indicate a progressively decreasing trend in a continuum of data from healthy, young bone to stiffer bone in individuals having osteoarthritis, to even more stiff and brittle bone in individuals having osteoporosis. (See FIG. 2). Damping values are significantly different for all comparisons (p values ranging between 0.04 and 0.0001), except between healthy adults and healthy youth and individuals with osteoporosis without fracture and individuals with osteoarthritis. The data show that individuals with degenerative skeletal disorders have significantly decreased bone shock absorbing capacity, as compared to normal healthy subjects.

Example 3

Damping Values at the Site of Fracture

The data from the two groups of Caucasian post-menopausal female subjects of Example 2 are further considered (osteoporosis with fracture, N=28 and osteoporosis without fracture, N=39) in order to demonstrate the differences in damping values between groups at the site of fracture. The site of fracture was between the third lumbar vertebra (lower back) and the seventh thoracic vertebra (upper back). The absolute damping value of the fracture group was significantly lower than that of the non-fracture group for lower back (p=0.003) as well as for the upper back regions (p=0.009) (see FIG. 1). The absolute damping values for the fracture group due to heel-strike at the fracture sites (damping value at upper back: 1.26 and at lower back: 3.15) were significantly lower than that at tibia (damping value=5.3) and femoral (damping value=5.1) bone sites (data not shown). The results indicate that osteoporosis has a more detrimental impact on damping properties of the bone at the fracture site as compared to non-fracture sites (see FIGS. 1 and 2).

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A computer system for assessing dynamic bone quality, the system comprising:
   a memory that stores executable instructions;
   a central processing unit (CPU) capable of accessing the memory and executing the instructions to provide an output; and
   a receiver for receiving data input and transmitting the data input to the CPU; wherein the receiver is operably connected to:
   (1) at least one accelerometer, contacting an exterior surface of a human subject with each at least one accelerometer located at a respective anatomical site of the human subject to generate acceleration response data indicative of a rate of change of velocity at each respective site of contact; and
   (2) a force plate adapted to generate vertical ground reaction force data that is indicative of a heel strike on the force plate;
   wherein the CPU receives the acceleration response data from the at least one accelerometer and the vertical ground reaction force data from the force plate and executes the instructions to transform the acceleration response data and the vertical ground reaction force data into a bone damping value by:
   i) determining a Fast Fourier Transform (FFT) of the vertical ground reaction force data and a FFT for each of the acceleration response data sets received from each of the at least one accelerometer located at an anatomical site of interest; and
   ii) determining a Frequency Response Function (FRF) for each of the anatomical sites by dividing the FFT of the vertical ground reaction force data by the respective FFT acceleration response data collected from the respective at least one accelerometer at each anatomical site.

2. The computer system of claim 1, further comprising an accelerometer adapted to contact an exterior surface of the human subject at a non-load-bearing anatomical site of the human subject, wherein the further accelerometer is operably connected to the receiver.

3. The computer system of claim 1, wherein the load-bearing anatomical sites are selected from the group consisting of the shins, the tibias, the femurs, and the vertebrae.

4. The computer system of claim 1, wherein the at least one accelerometer is selected from the group consisting of wired accelerometers, wireless accelerometers, MEMS based nano-accelerometers, and combinations thereof.

5. The computer system of claim 2 wherein the further accelerometer is selected from the group consisting of wired accelerometers, wireless accelerometers, MEMS based nano-accelerometers, and combinations thereof.

6. The computer system of claim 1, wherein the receiver is operably connected to a plurality of accelerometers.

7. The system of claim 1, wherein at least one accelerometer is adapted to contact the exterior surface of the human subject at a point selected from the group consisting of at the lower portion of the shin above an ankle, at a third lumbar vertebra, and at a seventh thoracic vertebra.

8. The system of claim 2, wherein the further accelerometer is adapted to contact the exterior surface of the human subject at a head.

9. The system of claim 2, wherein the further accelerometer is adapted to contact the exterior surface of the human subject at a forehead.

10. The system of claim 6, wherein the plurality of accelerometers comprises a first accelerometer contacted to the exterior surface of the human subject at the shin, a second accelerometer contacted to the exterior surface of the human subject at the tibia, a third accelerometer contacted to the exterior surface of the human subject at the femur, a fourth accelerometer contacted to the exterior surface of the human subject at the vertebra, and a fifth accelerometer contacted to the exterior surface of the human subject at the vertebra when the acceleration response data is generated.

11. The computer system of claim 6 wherein after determining a Frequency Response Function (FRF) for each of the anatomical sites, the CPU transforms the Frequency Response Functions (FRF) for each of the anatomical sites by:
    iii) determining a bone damping value directly from the measured FRF for each of the anatomical sites by using a structural bandwidth and resonance frequency method to transform the Frequency Response Function (FRF) into the bone damping value at that anatomical site.

12. The computer system of claim 11 wherein the step of using the structural bandwidth and resonance frequency method to transform the Frequency Response Function (FRF) into the bone damping value further comprises:
    iv) determining the structural bandwidth manifest in a FRF real part as the frequency separation between two extrema that are symmetric about the resonance frequency, and determining the resonance frequency which coincides with a single peak in the FRF imaginary part to determine the bone damping value for each anatomical site.

13. The computer system of claim 12 wherein after the step of determining the structural bandwidth manifest in the FRF real part and the resonance frequency in the FRF imaginary part, the CPU transforms the structural bandwidth manifest in the FRF real part and the resonance frequency in the FRF imaginary part into a bone damping value by:
    v) dividing the structural bandwidth by the resonance frequency, and dividing the result by one half.

14. The computer system of claim 1, wherein the dynamic bone quality is assessed by:
    comparing the bone dampening value determined at an anatomical site of interest to a reference bone damping value at the same site of interest obtained from one or more normal healthy adults.

* * * * *